United States Patent [19]

Lampert

[11] 4,280,495
[45] Jul. 28, 1981

[54] AIR EMBOLI DETECTION

[75] Inventor: Seymour R. Lampert, Ann Arbor, Mich.

[73] Assignee: Sarns, Inc., Ann Arbor, Mich.

[21] Appl. No.: 963,311

[22] Filed: Nov. 24, 1978

[51] Int. Cl.³ .............................................. A61M 5/14
[52] U.S. Cl. .................... 128/214 E; 422/45; 210/94
[58] Field of Search .......... 128/214 R, 214 C, 214 E, 128/214 F, DIG. 3, DIG. 13; 73/19, 194 E, DIG. 11; 250/573; 356/39, 410–411; 137/177; 340/603, 608, 630, 632; 422/44–48; 210/85–86, 94

[56] References Cited

U.S. PATENT DOCUMENTS

| 3,812,482 | 5/1974 | Clark | 128/214 E |
|---|---|---|---|
| 3,846,772 | 11/1974 | Peberdy | 340/630 |
| 3,896,803 | 7/1975 | Mason | 128/214 R |
| 3,935,876 | 2/1976 | Massie et al. | 128/214 F |
| 3,989,625 | 11/1976 | Mason | 128/214 E |
| 4,038,982 | 8/1977 | Burke et al. | 128/214 E |
| 4,114,144 | 9/1978 | Hyman | 128/DIG. 13 |
| 4,124,301 | 11/1978 | Pocock | 250/573 |
| 4,155,362 | 5/1979 | Jess | 128/214 F |
| 4,164,937 | 8/1979 | Spencer | 128/666 |
| 4,166,961 | 9/1979 | Dam et al. | 250/573 |
| 4,167,331 | 9/1979 | Nielsen | 128/633 |
| 4,181,610 | 1/1980 | Shintani et al. | 128/214 E |

FOREIGN PATENT DOCUMENTS 2379290  10/1978  France ..................... 128/214 E Primary Examiner—Robert W. Michell
Assistant Examiner—Francis J. Jaworski
Attorney, Agent, or Firm—Barnes, Kisselle, Raisch & Choat

[57] ABSTRACT

Air emboli detection method and apparatus for use in cardiopulmonary bypass surgery or the like comprising modular sensor, control and power units. The sensor unit is adapted to releasably clamp a blood flow tubing or conduit in a vertical orientation below a blood deaerator, and includes an LED infrared source and a phototransistor detector. The control unit applies pulsed power to the light source only at preselected periodic intervals, and monitors for an output from the detector only at times corresponding to the preselected intervals to achieve an enhanced signal-to-noise ratio. The power unit includes a solid state relay responsive to detection of emboli for removing power from a blood pump or the like.

4 Claims, 2 Drawing Figures

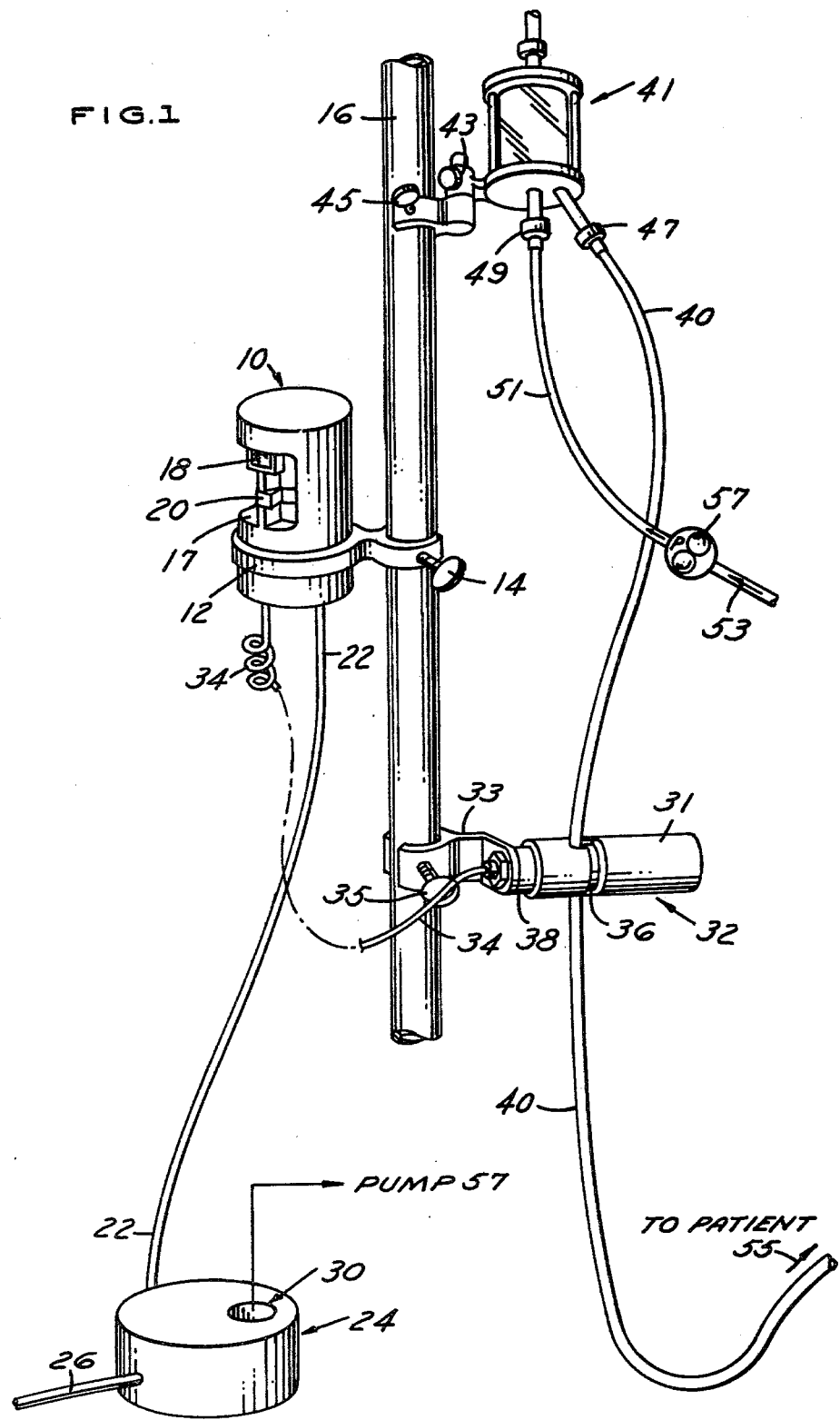

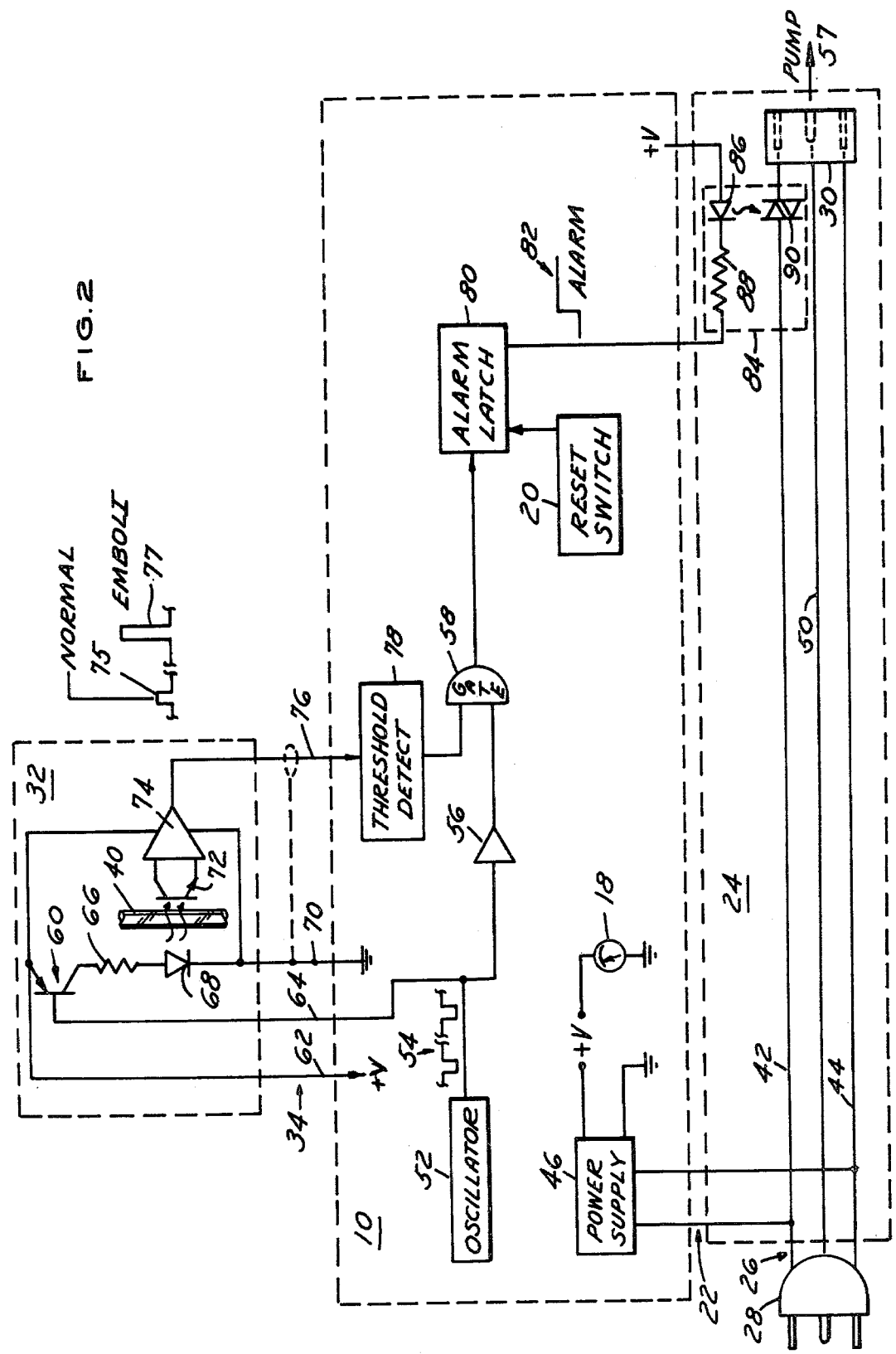

AIR EMBOLI DETECTION

The present invention relates to surgical monitoring and control techniques, and more particularly to an air bubble or emboli detection apparatus and methods in cardiopulmonary bypass surgery or the like.

Objects of the present invention are to provide an air emboli detection apparatus which is modular in construction and therefore highly flexible in installation, which embodies state-of-the-art solid state control techniques and therefore is economical in assembly and reliable in operation, and/or which possesses an enhanced signal-to-noise ratio as compared with emboli detection techniques of the prior art.

The invention, together with additional objects, features and advantages thereof, will be best understood from the following description, the appended claims and the accompanying drawings in which:

FIG. 1 is a fragmentary elevational view illustrating the modular detection apparatus provided by the invention; and FIG. 2 is a partially schematic and partially functional block diagram of a presently preferred embodiment of the detection apparatus provided by the invention.

Referring to FIG. 1, a presently preferred embodiment of the modular apparatus provided by the invention includes a control unit 10 carried by a clamp 12 for adjustable positioning by means of a thumbscrew 14 on a bed post or stanchion 16. Modular control unit 10 includes an open window 17 for viewing a voltage meter 18, and for providing access to a reset rocker switch 20. Other circuitry included within control unit 10 will be described hereinafter in connection with FIG. 2. Unit 10 is connected by an extensible coiled cord 22 to a power relay unit 24. A power cord 26 extends from relay unit 24 and terminates in a plug 28 (FIG. 2) for connection to a conventional wall outlet or the like. A female socket 30 is carried by relay unit 24 for supplying selectively controlled power to a blood pump illustrated schematically at 57.

A sensor unit 32 is connected by a second extensible coiled cord 34 to control unit 10, and includes an infrared source and detector (FIG. 2) for positioning on opposite sides of a blood flow path. More specifically, sensor unit 32 includes a cylindrical housing 31 having an L-shaped slot 36 opening radially laterally therefrom. A piston or plunger 38 extends axially from an open end of housing 31 and is mounted by a bracket 33 and a thumbscrew 35 to post 16. Housing 31 may be manually telescoped over plunger 38 against the force of an internal spring (not shown) until a laterally opening slot in the plunger (not shown) aligns with slot 36. A translucent tube or conduit 40 of PVC or the like may then be positioned within the aligned slots and will be captured within sensor unit 32 when spring-biased plunger 38 is released. The infrared source and detector (FIG. 2) are carried by plunger 38 and are disposed on opposite sides of conduit 40 when the conduit is removably clamped within the sensor unit 32 as illustrated in FIG. 1. The mechanical structure of sensor unit 32 itself is illustrated in U.S. Pat. No. 4,091,672 assigned to the assignee hereof.

Sensor unit 32 is clamped in fixed position on post 16 with slot 36 oriented such that conduit 40 is held fixedly therein. A bubble trap or deaerator 41 is clamped to post 16 by a bracket 43 and a thumbscrew 45 above sensor unit 32. Conduit 40 is connected to an outlet fitting 47 in the lower portion of trap 47, and a corresponding inlet fitting 49 is connected by a second conduit 51 to receive blood from a pump 57 in flow direction 53. After passage through sensor unit 32, conduit 40 may be fed to a patient (not shown) with the direction of blood flow being indicated at 55. It will be noted that conduit 40 has a substantial vertical stretch below sensor 32, such stretch being preferably at least ten inches in length. Bubble trap 41 may comprise any conventional blood deaeration device such as that marketed by the assignee hereof and designated by model number 6302.

Thus, in accordance with one important feature of the invention, bubble trap 41 and sensor 32 are so positioned relative to each other as to cause the blood to flow vertically downwardly through the sensor unit. This important feature possesses two distinct advantages: (1) Any air bubbles in the blood stream will remain intact and approximately spherical, and will tend to flow in the center of the stream. Such bubbles may be readily detected by the sensor when on the order of 1cc or larger. If the flow path were horizontal or at an angle, however, air bubbles would flow along a tube inner wall, which would tend to stretch and break up the bubbles and thereby render detection less reliable. (2) When an air bubble is detected and pump 57 is shut off, the bubble will then tend naturally to migrate upwardly in conduit 40 both away from the patient and toward the bubble trap 41.

Referring to FIG. 2, the hot and neutral power lines 42, 44 in power relay unit 24 from cable 26 are connected by cable 22 to a d.c. power supply 46 in control unit 10. Meter 18 illustrates operation of power supply 46 to an observer. Neutral line 44, together with the ground line 50 from cable 26, is additionally connected in relay unit 24 to the corresponding terminals in socket 30. Control unit 10 includes an oscillator 52 for supplying pulsed control signals illustrated at 54 at preselected periodic intervals. Preferably, the low or zero-level portions of control signal 54 have durations in the range of fifty to seventy microseconds, with the portions occurring at intervals in the range of 1 to 1.2 milliseconds. In a preferred embodiment of the invention, the zero-level portions of the control signal have a duration on the order of fifty microseconds and occur at intervals on the order of one millisecond. Oscillator 52 is connected in control unit 10 through an inverter 56 to one input of a gate 58.

Sensor 32 includes a PNP transistor 60 having an emitter connected by one conductor 62 in cable 34 to the positive voltage output of power supply 46. The base of transistor 60 is connected by a second conductor 64 in cable 34 to the pulsed control output of oscillator 52. The collector of transistor 60 is connected through a current limiting resistor 66 and an LED 68, and then to ground in control unit 10 through a third cable conductor 70. LED 68 is optically coupled through tubing 40 to a phototransistor 72 which is connected to a differential amplifier 74. The pulsed output of amplifier 74 is connected through a fourth cable conductor 76 and a threshold detection circuit 78 in control unit 10 to a second input of gate 58. Amplifier 74 receives power and ground inputs from conductors 62 and 70 respectively. Thus, in accordance with an important aspect of the present invention, modular sensor unit 32 includes a constant current drive transistor 60 for the LED light source 68 and a first-stage amplifier 74 for phototransistor 72, and is connected to control unit 10 only by means of the four conductor cable 34 as previously described. It will be appreciated, of course, that the pulsed output of amplifier 74 is normally at a relatively low level 75 when only blood is present in conduit 40, but reaches a higher level 77 above the factory adjusted threshold of detector 78 when one or more air bubbles or emboli are within tubing 40 between the LED and the phototransistor.

The output of gate 58 in control unit 10 is connected to an alarm latch 80 for providing an alarm condition signal illustrated at 82 whenever the pulsed output of amplifier 74 exceeds the detection threshold of circuit 78. The output of alarm latch 80 is connected by cable 22 to a solid state relay 84 in power relay unit 24. Relay 84 includes an LED relay sensor 86 connected to the positive voltage output of power supply 46 by cable 22, and a current limiting resistor 88 connected between the cathode of LED 86 and the alarm latch output. An optical triac relay switch 90 is connected between a.c. hot line 42 and the corresponding terminal in socket 30. Thus, current is conducted through LED 86 during the normally low output condition of alarm signal 82, such that the triac 90 is normally conducting. Switching of the alarm output to a high condition, indicative of a detected air bubble or embolus, blocks current conduction through LED 86 and therefore renders triac 90 open or nonconductive, thereby removing power from blood pump 57 as previously described. Reset switch 20 (FIGS. 1 and 2) is connected to reset latch 80, and thereby supply power to the blood pump, when the emboli alarm condition has been corrected.

It will be appreciated in accordance with another important feature of the present invention that pulsed energization of infrared LED 68 only at preselected periodic intervals, coupled with selective gating of the detector output via inverter 56 and gate 58 only at times corresponding to the preselected intervals, yields a signal-to-noise ratio which is significantly enhanced as compared with the steady or constant illumination techniques indicative of the prior art. More specifically, pulsed rather than steady state energization of LED 68, which has an optical output preferably at a wavelength of on the order of 0.9 microns, permits the diode to be driven harder and thereby yield greater light energy for short periods of time than would otherwise be possible with steady state energization. Thus, the optical output of LED 68 during the gating window is significantly enhanced. An improvement to signal-to-noise ratio by a factor of twenty-to-one has been experienced in detection units embodying the invention.

The advantageous positioning and relative orientation of the bubble trap, sensor and blood flow path illustrated in FIG. 1 is the subject of the copending application of Phillip J. Teders, Ser. No. 963,312 filed concurrently herewith and assigned to the assignee hereof.

The invention claimed herein is:

1. In apparatus for use in cardiopulmonary bypass surgery or the like and including a blood pump, means coupled to said pump for providing an extracorporeal blood flow path and sensor means disposed adjacent said path for detecting emboli in said path and coupled to said pump for deactivating said pump upon detection of any said emboli, said sensor means comprising a light source and light detection means disposed adjacent to said path and alarm means responsive to light incident upon said detection means from said source for indicating emboli in said path and deactivating said pump, the improvement wherein said sensor means further comprises electrical power supply means for energizing said source only at preselected periodic intervals with said source being otherwise de-energized and gate means electrically connected to said detection means, said power supply means and said alarm means for monitoring said detection means and enabling operation of said alarm means responsive to said detection means only at preselected times corresponding to said preselected periodic intervals.

2. The apparatus set forth in claim 1 wherein said supply means comprises an oscillator for energizing said source for durations of fifty microseconds at one millisecond intervals.

3. The apparatus set forth in claim 2 or 1 wherein said preselected periodic intervals comprise durations of source energization in the range of 50 to 70 microseconds at intervals in the range of 1 to 1.2 milliseconds.

4. In a process for controlling blood circulation during cardiopulmonary bypass surgery or the like comprising the steps of: (a) pumping blood through an extracorporeal translucent blood path, (b) monitoring for an emboli in said path by positioning a source of infrared energy and an infrared detector on opposite sides of said blood path and detecting any said emboli as a function of energy incident upon said detector from said source, and (c) terminating pumping in said step (a) in response to any such detected emboli, a method of improving the signal-to-noise ratio at said detection means comprising the steps of: (d) pulsing said source only at preselected periodic intervals and (e) monitoring for infrared energy at said detector indicative of air emboli in said extracorporeal path only at preselected times corresponding to said preselected periodic intervals.

* * * * *